(12) United States Patent
Chilukuri et al.

(10) Patent No.: US 9,562,844 B2
(45) Date of Patent: Feb. 7, 2017

(54) SYSTEMS AND DEVICES FOR SENSING CORROSION AND DEPOSITION FOR OIL AND GAS APPLICATIONS

(71) Applicant: Baker Hughes Incorporated, Houston, TX (US)

(72) Inventors: Anusha Chilukuri, Katy, TX (US); Othon R. Monteiro, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 260 days.

(21) Appl. No.: 14/319,158

(22) Filed: Jun. 30, 2014

(65) Prior Publication Data

US 2015/0377765 A1  Dec. 31, 2015

(51) Int. Cl.

| | |
|---|---|
| *G01N 21/00* | (2006.01) |
| *G02B 6/00* | (2006.01) |
| *G01N 17/04* | (2006.01) |
| *E21B 47/00* | (2012.01) |
| *E21B 47/12* | (2012.01) |
| *G01B 11/06* | (2006.01) |

(52) U.S. Cl.
CPC ............. *G01N 17/04* (2013.01); *E21B 47/00* (2013.01); *E21B 47/123* (2013.01); *G01B 11/0675* (2013.01)

(58) Field of Classification Search
CPC .......... G01L 1/246; G01N 17/04; G02B 6/022
USPC ..................................... 356/73.1; 382/12, 13
See application file for complete search history.

(56) References Cited

U.S. PATENT DOCUMENTS

| | | | |
|---|---|---|---|
| 5,299,271 | A | 3/1994 | Hildebrand |
| 5,367,583 | A | 11/1994 | Sirkis |
| 5,646,400 | A | 7/1997 | Perez et al. |
| 6,389,187 | B1 | 5/2002 | Greenaway et al. |
| 6,807,325 | B1 | 10/2004 | Kraemmer et al. |
| 6,888,623 | B2 | 5/2005 | Clements |
| 7,104,331 | B2 | 9/2006 | Bussear et al. |
| 7,199,869 | B2 | 4/2007 | MacDougall |
| 7,379,631 | B2 | 5/2008 | Poland et al. |
| 7,515,781 | B2 | 4/2009 | Chimenti et al. |

(Continued)

OTHER PUBLICATIONS

International Search Report for International Application No. PCT/US2015/038331 dated Sep. 21, 2015, 3 pages.

(Continued)

*Primary Examiner* — Sunghee Y Gray
(74) *Attorney, Agent, or Firm* — TraskBritt (57) ABSTRACT

Sensing systems include a tube defining a Fabry-Perot cavity and an optical fiber including a distal end disposed within the Fabry-Perot cavity and a proximal end. A corrodible material caps the Fabry-Perot cavity. Devices for sensing corrosion of downhole equipment include an optical fiber with a corrodible material disposed over a distal end of the optical fiber. Systems for sensing a condition in equipment include an optical fiber with a fiber Bragg grating proximate a distal end thereof and a mass of sensor material coupled to the distal end of the optical fiber. The mass of sensor material is suspended from above the fiber Bragg grating. Other systems for sensing a condition in a wellbore include an optical fiber and a plurality of fiber Bragg gratings along a length thereof. A plurality of sensor materials are coupled to the optical fiber and surround respective fiber Bragg gratings.

17 Claims, 6 Drawing Sheets

(56) References Cited

U.S. PATENT DOCUMENTS

| | | | |
|---|---|---|---|
| 8,025,445 B2* | 9/2011 | Rambow | E21B 47/011 |
| | | | 385/147 |
| 8,210,252 B2 | 7/2012 | Martin et al. | |
| 2003/0118297 A1 | 6/2003 | Dunphy et al. | |
| 2006/0013523 A1 | 1/2006 | Childlers et al. | |
| 2007/0189658 A1* | 8/2007 | Maas | G01P 1/023 |
| | | | 385/12 |
| 2007/0286561 A1 | 12/2007 | Poland | |
| 2011/0110621 A1 | 5/2011 | Duncan et al. | |
| 2012/0132008 A1 | 5/2012 | Way et al. | |

OTHER PUBLICATIONS

International Written Opinion for International Application No. PCT/US2015/038331 dated Sep. 21, 2015, 7 pages.

* cited by examiner

SYSTEMS AND DEVICES FOR SENSING CORROSION AND DEPOSITION FOR OIL AND GAS APPLICATIONS

FIELD

Embodiments of the present disclosure relate to systems and devices for sensing corrosion and deposition in equipment for the exploration and production of oil and gas, including, without limitation, corrosion of tools and tool components and deposition of scale on tools and tool components used in wellbores and surface equipment.

BACKGROUND

Tools and instruments used for oil and gas exploration and production are often exposed to corrosive conditions, such as high temperatures, high pressures, reactive chemicals, and abrasive materials. Therefore, these tools corrode and degrade during use. In addition, scale (i.e., debris and materials from the wellbore or from fluids therein) may be deposited on tools used for exploration and production of oil and gas, which may foul the operation of the tools and create a flow restriction. Fiber optic sensors have several advantages over electro-mechanical sensors: they exhibit greater resistance to aggressive environments, exhibit a smaller footprint with single-point or multi-point measurements, exhibit immunity to electromagnetic noise, and are more resistant to mechanical vibration.

BRIEF SUMMARY

In some embodiments, the present disclosure includes wellbore sensing systems including a tube defining a Fabry-Perot cavity, an optical fiber, a corrodible material capping the Fabry-Perot cavity, and an analysis module. The optical fiber includes a distal end disposed within the Fabry-Perot cavity and a proximal end opposite the distal end. The analysis module is operatively coupled to the proximal end of the optical fiber, and is configured to sense and analyze a difference of a light signal resulting from a change in a distance between the corrodible material and the distal end of the optical fiber due to a change in thickness of the corrodible material.

In some embodiments, the present disclosure includes devices for sensing corrosion of downhole equipment, including at least one optical fiber comprising a distal end and a proximal end. The devices also include a corrodible material disposed over the distal end of the at least one optical fiber. An analysis module is operatively coupled to the proximal end of the at least one optical fiber. The analysis module is configured to sense and analyze differences in a light signal reflecting from the corrodible material.

In some embodiments, the present disclosure includes systems for sensing at least one condition in oil and gas exploration or production equipment, including at least one optical fiber, an analysis module, and a mass of sensor material. The at least one optical fiber includes a distal end, at least one fiber Bragg grating proximate the distal end, and a proximal end. The analysis module is coupled to the proximal end of the at least one optical fiber, and is configured to sense and analyze variations in light reflected from the at least one fiber Bragg grating. The mass of sensor material is coupled to the distal end of the at least one optical fiber. At least one surface of the mass of sensor material is exposed to an environment surrounding the distal end of the at least one optical fiber. The distal end of the at least one optical fiber with the mass of sensor material coupled thereto is suspended from above the fiber Bragg grating to induce stress on the fiber Bragg grating due to a weight of the mass of sensor material.

In some embodiments, the present disclosure includes devices for sensing deposition of material on downhole equipment. The devices include at least one optical fiber comprising a proximal end and a distal end including a fiber Bragg grating. An analysis module is operatively coupled to the proximal end of the at least one optical fiber, and the analysis module is configured to sense and analyze variations in light reflected from the at least one fiber Bragg grating. The devices also include a suspension element coupled to the at least one optical fiber above the fiber Bragg grating. A mass of inert material is coupled to the at least one optical fiber below the fiber Bragg grating and suspended from the suspension element by the distal end of the at least one optical fiber.

In some embodiments, the present disclosure includes additional systems for sensing at least one condition in a subterranean wellbore. The systems include at least one optical fiber including a distal end, a plurality of fiber Bragg gratings along a length thereof, and a proximal end. A plurality of sensor materials are coupled to the at least one optical fiber and surround respective fiber Bragg gratings of the plurality of fiber Bragg gratings. A light wavelength sensor is coupled to a proximal end of the at least one optical fiber. The light wavelength sensor is configured to sense a wavelength of light reflected from the plurality of fiber Bragg gratings.

DETAILED DESCRIPTION

The following description provides specific details, such as material types, configurations, and operating conditions in order to provide a thorough description of embodiments of the present disclosure. However, a person of ordinary skill in the art will understand that the embodiments of the present disclosure may be practiced without employing these specific details. Indeed, the embodiments of the present disclosure may be practiced in conjunction with conventional techniques and materials employed in the industry.

In the following detailed description, reference is made to the accompanying drawings, which form a part hereof, and in which is shown, by way of illustration, specific embodiments in which the present disclosure may be practiced. These embodiments are described in sufficient detail to enable a person of ordinary skill in the art to practice the present disclosure. However, other embodiments may be utilized, and structural, logical, and electrical changes may be made without departing from the scope of the disclosure. The illustrations presented herein are not meant to be actual views of any particular system, device, structure, or process, but are idealized representations that are employed to describe the embodiments of the present disclosure. The drawings presented herein are not necessarily drawn to scale.

Similar structures or components in the various drawings may retain the same or similar numbering for the convenience of the reader; however, the similarity in numbering does not mean that the structures or components are necessarily identical in size, composition, configuration, or other property.

As used herein, the term "substantially" in reference to a given parameter, property, or condition means and includes to a degree that one skilled in the art would understand that the given parameter, property, or condition is met with a small degree of variance, such as within acceptable manufacturing tolerances. For example, a parameter that is substantially met may be at least about 90% met, at least about 95% met, or even at least about 99% met.

As used herein, any relational term, such as "first," "second," "over," "top," "bottom," "underlying," etc., is used for clarity and convenience in understanding the disclosure and accompanying drawings and does not connote or depend on any specific preference, orientation, or order, except where the context clearly indicates otherwise.

As used herein, the term "corrosion" means physical and chemical degradation.

As used herein, the term "corrodible" in reference to a material means susceptible to corrosion in an environment in which the material is to be placed.

As used herein, the term "distal" refers to a portion of a structure or a location that is relatively more distant from an indicated point of reference than another portion of a structure or another location.

As used herein, the term "proximal" refers to a portion of a structure or a location that is relatively closer to an indicated point of reference than another portion of a structure or another location.

The embodiments of the present disclosure include fiber optic sensors for sensing corrosion, scale deposition, and the presence of reactive chemicals in harsh environments, such as in wellbores formed in the earth for exploration for and production of hydrocarbons such as oil and natural gas, as well as exploration for and production of geothermal energy. In some embodiments, single-point sensors are disclosed Referring to FIG. 1, an embodiment of a wellbore sensing system 100 is shown. The wellbore sensing system 100 includes downhole components 102 within a wellbore 104. In embodiments in which the wellbore 104 was previously formed (e.g., during oil production), the downhole components 102 may include production components, such as an electric submersible pump ("ESP") 106 and casing 108. In embodiments in which the wellbore 104 is being formed (during, e.g., oil exploration or wellbore formation), the downhole components 102 may include earth-boring components, such as a downhole motor, an earth-boring tool, and drill pipe. In either case, the downhole components 102 may be exposed to a corrosive environment including one or more of high temperatures, high pressures, abrasive materials, and reactive chemicals, for example.

The wellbore sensing system 100 may include a sensor including at least one optical fiber 110 having at least one sensing point 112. For example, a single-point sensor may include a single sensing point 112A at a distal end 114 of the at least one optical fiber 110. By way of another example, a multi-point sensor may include a plurality of sensing points 112B along a length of the at least one optical fiber 110. Embodiments of both single-point and multi-point sensors will be described in more detail below with reference to FIGS. 2-6.

Figure 1:
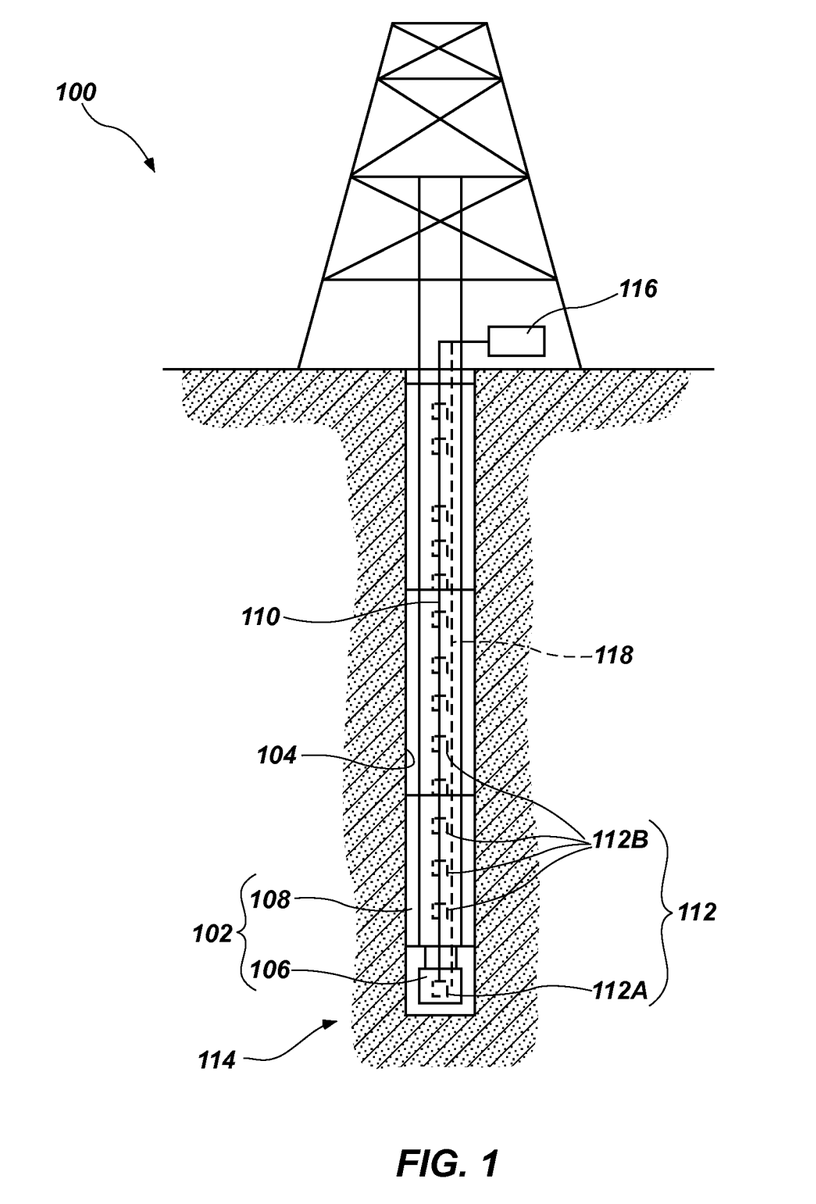
FIG. 1 illustrates an embodiment of a wellbore sensing system according to the present disclosure.

The wellbore sensing system 100 may include an analysis module 116 operably coupled to the at least one optical fiber 110. The analysis module 116 may be configured to receive and analyze signals in the form of light (e.g., visible light, infrared light, ultraviolet light) reflected and/or refracted from the at least one sensing point 112. For example, the analysis module 116 may include a frequency domain reflectometer. Frequency domain reflectometers are commercially available, such as the "Luna Distributed Sensing System" sold by Luna Innovations Incorporated of Roanoke, Va. U.S. patent application Ser. No. 11/180,389 to Childers et al., titled "FIBER OPTIC POSITION AND SHAPE SENSING DEVICE AND METHOD RELATING THERETO," filed on Jul. 13, 2005, describes operation of a fiber optic position and shape sensing device comprising an optical fiber means. A frequency domain reflectometer is positioned in an operable relationship to the optical fiber means. The disclosure of U.S. patent application Ser. No. 11/180,389 is incorporated in its entirety herein by reference. By way of other examples, the analysis module 116 may include at least one of a light source, a photodetection and signal processing interferometer, a light wavelength sensor, a light intensity sensor, and an output configured to provide a signal (e.g., an electronic signal, a display, data) corresponding to the metric to be measured (e.g., corrosion rate).

Optionally, one or more reference optical fibers 118 (as shown by dashed line) may be positioned proximate and along the at least one optical fiber 110 to compensate for changes in temperature, pressure, stress (such as, for example, bending, compressive, tensile, and torsional stress), vibrations, etc., and to provide a reference signal that can be compared to (e.g., subtracted from) a signal from the at least one optical fiber 110 to determine a portion of the signal from the at least one optical fiber 110 that correlates to the condition to be sensed, independent of other conditions to which the at least one optical fiber 110 and the one or more reference optical fibers 118 are exposed. For example, U.S. patent application Ser. No. 11/451,207 to Poland et al., titled "MULTI-CORE DISTRIBUTED TEMPERATURE SENSING FIBER," filed on Jun. 12, 2006, now U.S. Pat. No. 7,379,631, issued May 27, 2008, describes a multi-core distributed temperature sensing optical fiber, wherein the arrangement and construction of at least two cores provides a spectral attenuation corrected (e.g., corrected for hydrogen and/or stress on the fiber) temperature measurement. The disclosure of U.S. Pat. No. 7,379,631 is incorporated in its entirety herein by reference.

The wellbore sensing system 100 of the present disclosure may be configured to provide a signal relating to, for example, one or more of temperature, stress, strain, pressure, occurrence of corrosion, rate of corrosion, presence of a reactive chemical, and position information at the at least one sensing point 112, as will be further explained below.

Figure 2:
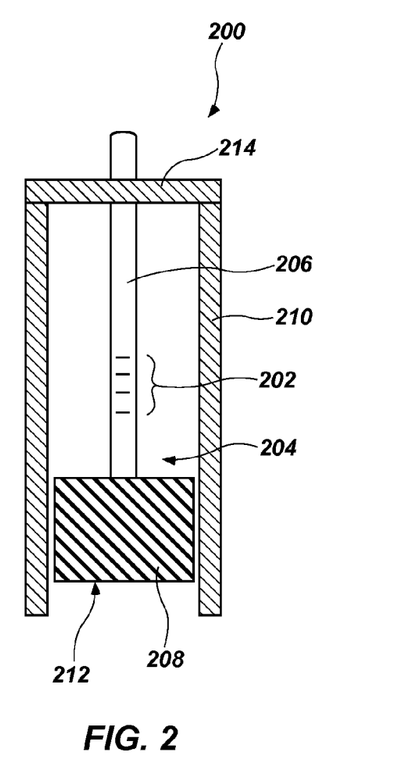
FIG. 2 shows a partial cross-sectional view of an embodiment of a fiber optic sensor according to the present disclosure.

Referring to FIG. 2, wellbore sensing systems of the present disclosure may include a fiber optic sensor 200 including a fiber Bragg grating 202 proximate a distal end 204 of an optical fiber 206 and a mass of sensor material 208 coupled to the distal end 204 of the optical fiber 206. A housing 210 may cover lateral sides of the mass of sensor material 208, while leaving at least a portion of an end surface 212 of the mass of sensor material 208 exposed to the surrounding environment. The distal end 204 of the optical fiber 206 and the mass of sensor material 208 may be suspended from a suspension element 214, such that the fiber Bragg grating 202 is positioned between the suspension element 214 and the mass of sensor material 208. The mass of sensor material 208 may be restricted from moving laterally (e.g., to the left and right and into and out of the page from the perspective of FIG. 2), but not restricted from moving axially (e.g., up and down from the perspective of FIG. 2) by the housing 210. Thus, the weight of the mass of sensor material 208 may physically stress (e.g., stretch) the portion of the optical fiber 206 including the fiber Bragg grating 202 between the suspension element 214 and the mass of sensor material 208.

Optical fibers including fiber Bragg gratings are known in the art and are described in, for example: U.S. patent application Ser. No. 09/979,345 to Kraemmer et al., titled "BRAGG GRATING DEVICE FOR MEASURING AN ACCELERATION," issued as U.S. Pat. No. 6,807,325 on Oct. 19, 2004; U.S. patent application Ser. No. 11/180,389 to Childers et al., titled "FIBER OPTIC POSITION AND SHAPE SENSING DEVICE AND METHOD RELATING THERETO," filed Jul. 13, 2005; and U.S. patent application Ser. No. 11/451,207 to Poland et al., titled "MULTI-CORE DISTRIBUTED TEMPERATURE SENSING FIBER," filed on Jun. 12, 2006; the entire disclosure of each of which is incorporated herein by reference.

By way of example, the fiber Bragg grating 202 may include a portion of a core of the optical fiber 206 characterized by periodic variations in refractive index. The period of the fiber Bragg grating 202 (i.e., the distance between adjacent portions having variations in refractive index) results in reflection and/or refraction of light of a specific wavelength or range of wavelengths correlating to the period of the fiber Bragg grating 202. If the period of the fiber Bragg grating 202 is relatively larger, then light having a relatively longer wavelength will be reflected and/or refracted by the fiber Bragg grating 202. Conversely, if the period of the fiber Bragg grating 202 is relatively smaller, then light having a relatively shorter wavelength will be reflected and/or refracted by the fiber Bragg grating 202. An analysis module (e.g., the analysis module 116 described above with reference to FIG. 1) operatively coupled to the at least one optical fiber 206 can be used to sense the wavelength of light reflected and/or refracted by the fiber Bragg grating 202. A single fiber Bragg grating 202 may have a variable period (and, therefore, may reflect and/or refract light having a corresponding variable wavelength) that is dependent on the axial stretching and compressing of the optical fiber 206, which respectively increases and decreases the period of the fiber Bragg grating 202. Axial stretching and compressing of the optical fiber 206 may result from, for example, changes in temperature of and axial physical stress on the optical fiber 206.

The fiber optic sensor 200 shown in FIG. 2 may be used to sense corrosion of the mass of sensor material 208 due to chemical and/or physical degradation of the end surface 212 of the mass of sensor material 208. As material from the mass of sensor material 208 is exposed to a corrosive environment and corroded, the weight of the mass of sensor material 208 may be reduced, which may reduce stress on the optical fiber 206 resulting from the weight of the mass of sensor material 208. As a result, the period of the fiber Bragg grating 202 may be reduced as the stress thereon is relaxed. A signal (e.g., light reflected and/or refracted) from the fiber Bragg grating 202 may be altered due to the change in the period of the fiber Bragg grating 202. The signal may be sensed remotely by an analysis module coupled to a proximal end of the optical fiber 206, and the change in the signal may be correlated to corrosion of the mass of sensor material 208. Thus, the fiber optic sensor 200 may be used to remotely sense corrosion at the distal end 204 of the optical fiber 206. The fiber optic sensor 200 may be a single-point sensor for sensing corrosion at a single point within a wellbore (e.g., at a position of the distal end 204 of the optical fiber 206). In some embodiments, multiple fiber optic sensors 200 may be used within a single wellbore to sense corrosion at multiple points within the wellbore.

In use within a wellbore, the fiber optic sensor 200 may be positioned proximate a downhole component, such as by coupling the housing 210 to the downhole component or simply by extending the fiber optic sensor 200 into the wellbore to the position of the downhole component. The material of the mass of sensor material 208 may include a corrodible material that is selected to have a corrosion rate that is at least substantially the same as a corrosion rate of a material of the downhole component. In some embodiments, the material of the mass of sensor material 208 may be the same as the material of the downhole component. By way of example and not limitation, the material of the mass of sensor material 208 may include one or more of aluminum, titanium, a carbon steel, a tool steel, a stainless steel, and a so-called "corrosion-resistant alloy." Corrosion resistant alloys may include, for example, steels such as those identified in industry as 9 Cr-1 Mo, 13 Cr, 13 Cr-2 Mo, 416 stainless steel, 316 stainless steel, and nickel alloys such as those identified in industry as nickel alloy 625, nickel alloy 718, and MONEL® K-500. Thus, corrosion of the mass of sensor material 208 that is sensed by the fiber optic sensor 200 may be directly correlated to corrosion of the corresponding downhole component. The surface area of the mass of sensor material 208 end surface 212 may be known and used to calculate a corrosion rate of the material based on a mass loss over time detected by the fiber optic sensor 200. Thus, the fiber optic sensor 200 may be used to detect occurrence of corrosion and/or a corrosion rate of the downhole component.

In some embodiments, the fiber optic sensor 200 may additionally or alternatively be configured and used to sense deposition of scale on the downhole component. For example, if the material of the downhole component is susceptible to scale deposition, the material of the mass of sensor material 208 or a portion thereof may be selected to also be susceptible to scale deposition (e.g., by forming the mass of sensor material 208 of the same material as the downhole component). In operation, as scale is deposited on the end surface 212 of the mass of sensor material 208, a combined weight of the mass of sensor material 208 and deposited scale increases and induces greater tension on the fiber Bragg grating 202. The increased tension, in turn, increases the period of the fiber Bragg grating 202. A corresponding shift in wavelength of reflected and/or refracted light may be sensed and correlated to the scale deposition.

The mass of sensor material 208 may be formed of a substantially uniform and homogeneous material, or may be formed of a non-uniform and heterogeneous material. For example, in some embodiments, the mass of sensor material 208 may be formed of a substrate coupled to the distal end 204 of the optical fiber 206, with a material at least substantially similar to the material of the downhole component coupled to (e.g., attached to, sputtered on, bonded to, deposited on) the substrate.

The fiber optic sensor 200 of FIG. 2 has been described as including a single optical fiber 206. However, the present disclosure is not so limited. Rather, in some embodiments, multiple optical fibers 206 may be coupled to the mass of sensor material 208. In such embodiments, the mass of sensor material 208 may be larger than would be possible with a single optical fiber 206 because the multiple optical fibers 206 would, in combination, be capable of holding more weight without breaking. Therefore, the mass of sensor material 208 may include more material to corrode for longer operational life. In addition, respective signals from the multiple optical fibers 206 may be independently sensed and analyzed to identify non-uniform corrosion of the mass of sensor material 208.

Figure 3:
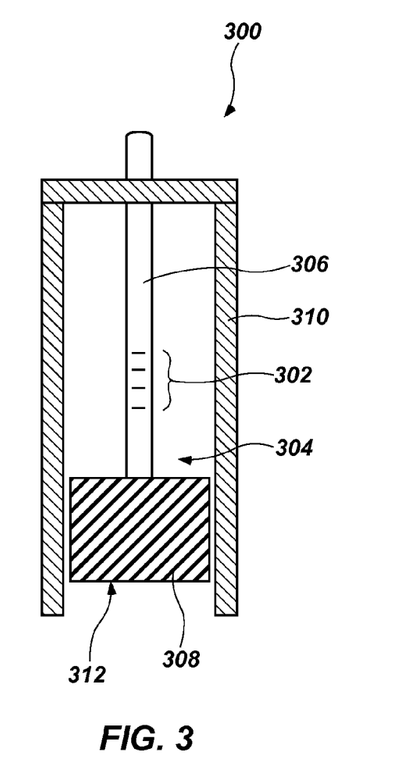
FIG. 3 shows a partial cross-sectional view of an embodiment of a reference fiber optic sensor according to the present disclosure.

Referring to FIG. 3 in conjunction with FIG. 2, in some embodiments, a reference fiber optic sensor 300 may be used with the fiber optic sensor 200. The reference fiber optic sensor 300 of FIG. 3 may be similar to the fiber optic sensor 200 described with reference to FIG. 2, and may include a fiber Bragg grating 302 proximate a distal end 304 of an optical fiber 306 and a housing 310, at least substantially as described above. However, the reference fiber optic sensor 300 may include a mass of material 308 with at least an end surface 312 including a material that is different from the mass of sensor material 208. For example, the mass of sensor material 208 of the fiber optic sensor 200 may be a corrodible material and the mass of material 308 of the reference fiber optic sensor 300 may be an inert material. By way of example and not limitation, the inert material may include one or more of a ceramic material, a diamond-like carbon ("DLC") material, an oxide material, a sapphire material, an alumina material, a silicon carbide material, a silicon material, and a metallic material (e.g., corrodible material or material similar to the corrodible material) but with the end surface 312 coated with an inert coating, such as DLC. The entire mass of material 308 of the reference fiber optic sensor 300 may be the inert material, or the end surface 312 of the mass of material 308 may be coated with the inert material. In some embodiments, the mass of material 308 may include or be coated with a material selected to resist scale deposition, such as a hydrophobic material.

The reference fiber optic sensor 300 may be used to compensate for temperature, pressure, vibration, and other conditions that may alter the period of the fiber Bragg gratings 202, 302 during use. For example, both the fiber optic sensor 200 and the reference fiber optic sensor 300 may be exposed to the same conditions (e.g., temperature, pressure, vibration), which may induce a substantially similar, if not identical, shift in the period of both of the fiber Bragg gratings 202, 302. However, the mass of sensor material 208 may corrode or experience scale deposition while the mass of material 308 of the reference fiber optic sensor 300 may not (or may to a lesser degree) corrode or experience scale deposition. Accordingly, a signal (e.g., light reflecting and/or refracting) from the reference fiber optic sensor 300 may be compared to (e.g., subtracted from) a signal from the fiber optic sensor 200 to isolate a portion of the fiber optic sensor 200 signal that results from a change in the mass of sensor material 208, independent of temperature, pressure, vibration, and other environmental conditions.

Figure 4:
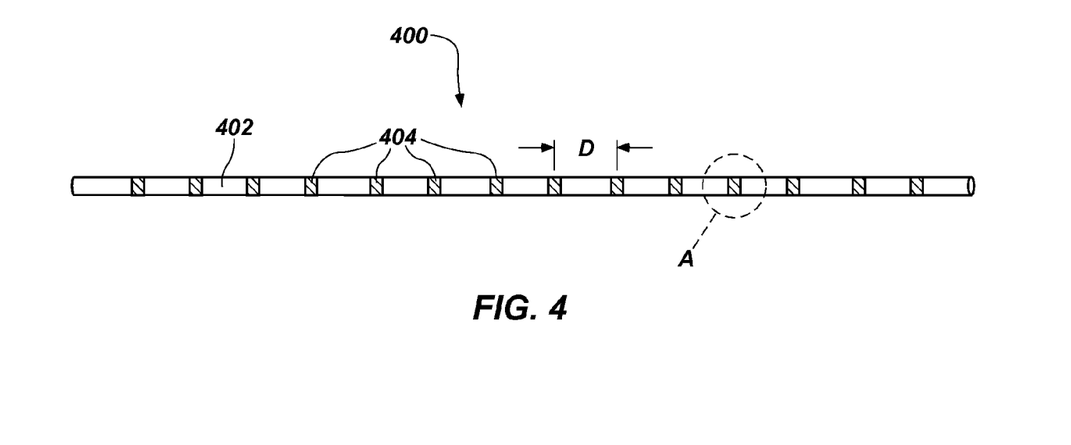
FIG. 4 shows a partial side view of an embodiment of a multi-point sensor according to the present disclosure.

Referring to FIG. 4, a multi-point sensor 400 may include an optical fiber 402 with multiple sensors 404 along a length thereof. Adjacent sensors 404 may be spaced at intervals D of, for example, at least about 5 mm, such as between about 5 mm and about 2 cm, although some embodiments of the present disclosure include sensors 404 at other intervals. The optical fiber 402 may be positioned in a wellbore to sense downhole conditions (e.g., temperature, pressure, presence of reactive chemical(s), corrosion rate) at multiple positions within the wellbore.

Figure 5:
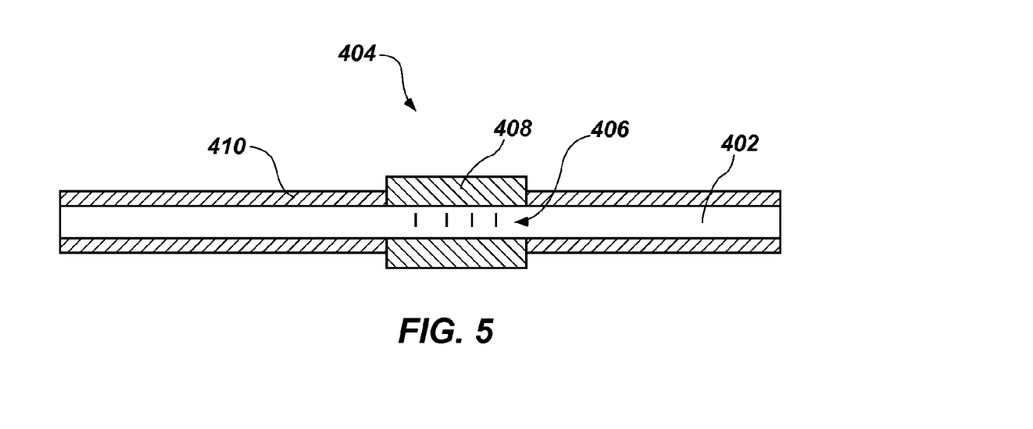
FIG. 5 shows a detailed cross-sectional view of a single sensor of the multi-point sensor of FIG. 4 within the dashed circle A.

FIG. 5 illustrates in detail the sensor 404 shown in FIG. 4 within dashed circle A. All of the sensors 404 of the multi-point sensor 400 shown in FIG. 4 may be substantially the same as the sensor 404 described below with reference to FIG. 5.

As shown in FIG. 5, each sensor 404 may be a portion of the optical fiber 402 that includes a fiber Bragg grating 406 surrounded by a sensor material 408. A cladding material 410 may surround the optical fiber 402 adjacent to the sensor material 408.

In some embodiments, the sensor material 408 may be or include a corrodible material, such as a material that is also used for a downhole component. The sensor material 408 may be pre-stressed in a manner that causes the fiber Bragg grating 406 to be in axial tension or compression. During use in a corrosive downhole environment, the sensor material 408 may corrode at a rate that is substantially the same as a corrosion rate of an exposed surface of a corresponding downhole component. As the pre-stressed sensor material 408 corrodes, the stress therein may relax and a period of the fiber Bragg grating 406 may be altered. A change in the period of the fiber Bragg grating 406 may be sensed and analyzed to determine a corrosion rate, in essentially the same manner as described above. Signals from each of the sensors 404 along the optical fiber 402 (FIG. 4) may be independently sensed and analyzed to identify localized corrosion.

In some embodiments, the sensor material 408 may be or include a material that is selected to sense a presence of a reactive chemical within the wellbore, such as hydrogen sulfide ($H_2S$), commonly termed "sour gas" in the industry. For example, the sensor material 408 may be selected to chemically react with the reactive chemical of interest. By way of example and not limitation, in embodiments in which the sensor 404 is intended for sensing the presence of $H_2S$, the sensor material 408 may be a metallic oxide material, such as zinc oxide (ZnO), which reacts with $H_2S$ to foini zinc sulfide (ZnS) and water ($H_2O$). The resulting ZnS has a volume that is theoretically about 59.18 times greater than a volume of ZnO. Accordingly, if the sensor material 408 of ZnO is exposed to sufficient $H_2S$, the sensor material 408 may expand and induce stress (e.g., tension) in the optical fiber 402, effectively stretching and increasing a period of the corresponding fiber Bragg grating 406. Thus, a signal from the sensor 404 may be remotely sensed and analyzed to identify the presence and location of $H_2S$ in the wellbore. In this manner, the multi-point sensor 400 may be used in a wellbore as a detection and warning system to enable identification of reactive chemicals prior to the reactive chemicals reaching a proximal portion of the wellbore. If a reactive chemical is sensed and located by the multi-point sensor 400, precautions or remedial action may be taken, such as shutting down production of the wellbore, shutting down production of a portion the wellbore, and/or evacuating personnel.

Figure 6:
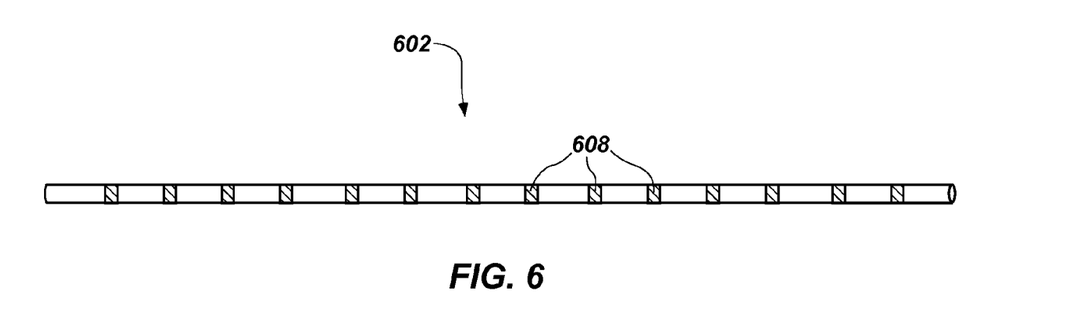
FIG. 6 shows a partial side view of an embodiment of a multi-point reference sensor according to the present disclosure.

Referring to FIG. 6 in conjunction with FIGS. 4 and 5, in some embodiments, the multi-point sensor 400 may be used with a reference optical fiber 602 that is similar to the optical fiber 402 described above, except that the sensor material 408 may be replaced by or coated with an inert (e.g., non-corrodible, non-reactive) material 608 in the reference optical fiber 602. As with the reference fiber optic sensor 300 (FIG. 3), the reference optical fiber 602 may be used to isolate portions of signals relating to the desired variable (e.g., corrosion rate, presence of a reactive chemical) from portions of signals resulting from other conditions (e.g., temperature, pressure, vibration).

Figure 7A:
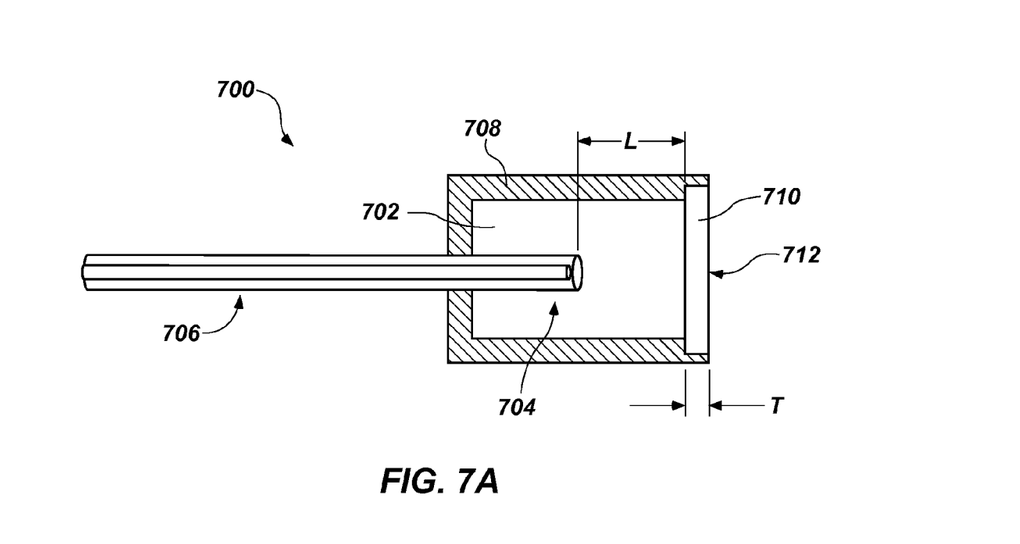
FIG. 7A shows a partial cross-sectional side view of another embodiment of a fiber optic sensor according to the present disclosure.

Referring to FIG. 7A, wellbore sensing systems of the present disclosure may include a fiber optic sensor 700 including a so-called Fabry-Perot cavity 702 at a distal end 704 of at least one optical fiber 706. The Fabry-Perot cavity 702 may be defined by a tube 708 (e.g., a capillary tube) capped with a corrodible material 710 having an external surface 712 that is configured for exposure to a corrosive environment, such as an environment within a subterranean wellbore or other fluid systems in oil and gas exploration and production. In some embodiments, an interior of the Fabry-Perot cavity 702 may be filled with a fluid, such as a liquid (e.g., oil) or a gas. The corrodible material 710 may be selected to include or be a similar (e.g., same) material as a downhole component proximate to the distal end of the at least one optical fiber 706, such that corrosion of the corrodible material 710 can be directly correlated to corrosion of the material of the downhole component. By way of example and not limitation, the corrodible material 710 may include one or more of a carbon steel, a tool steel, a stainless steel, and a so-called "corrosion-resistant alloy."

Extrinsic Fabry-Perot interferometry (EFPI) techniques may be used to measure the thickness of thin foils, such as of the corrodible material 710. The fiber optic sensor 700 of the present disclosure may operate by measuring the intensity and interference of light passing through the at least one optical fiber 706 and reflecting from the back-end of the corrodible material 710. As the external surface 712 of the corrodible material 710 is corroded by the corrosive environment to which the corrodible material 710 is exposed, an initial thickness T of the corrodible material 710 may diminish under a known pressure gradient across the corrodible material 710. Change in the thickness T under an applied pressure P (e.g., a fluid pressure) may cause a change in a gap length L between the distal end of the at least one optical fiber 706 and the back of the membrane, as illustrated in FIGS. 7B and 7C.

Figure 7B:
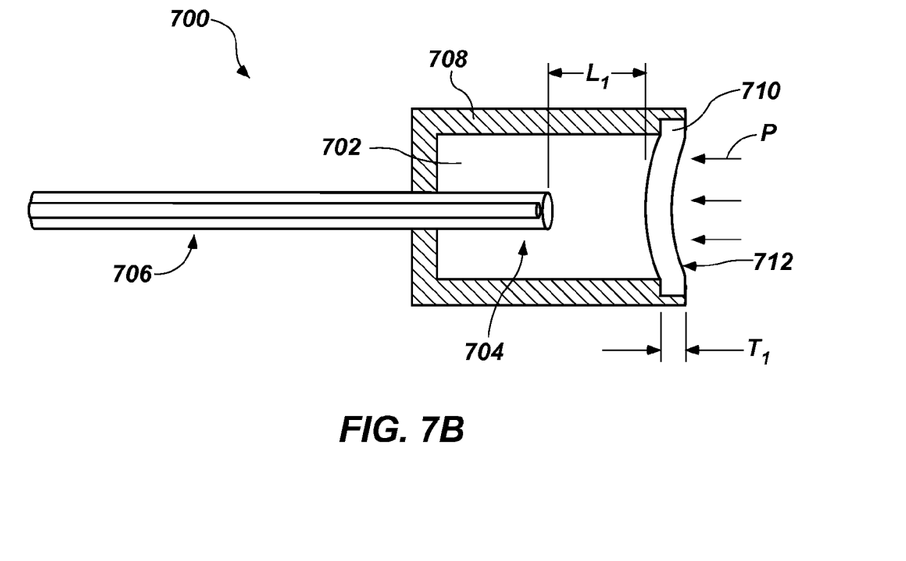
FIG. 7B shows a partial cross-sectional side view of the fiber optic sensor of FIG. 7A under pressure.
Figure 7C:
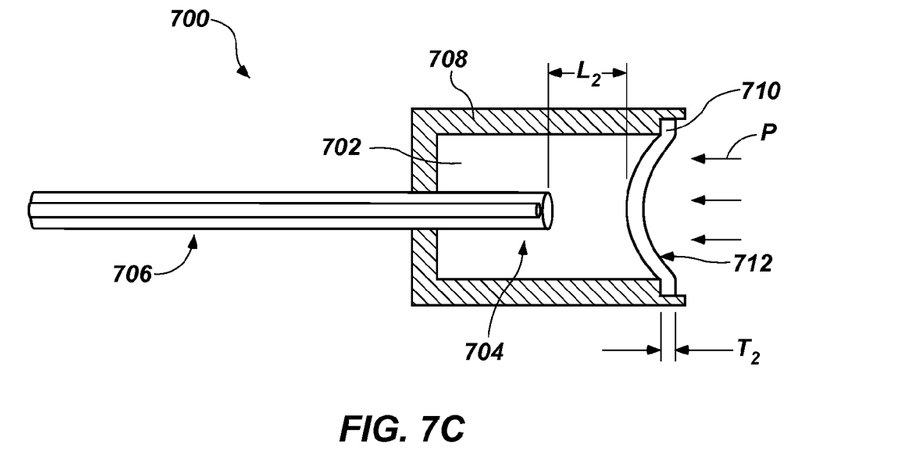
FIG. 7C shows a partial cross-sectional side view of the fiber optic sensor of FIG. 7A under pressure and after corrosion thereof.

As shown in FIGS. 7B and 7C, as a first thickness $T_1$ of the corrodible material 710 reduces due to corrosion of the external surface 712 thereof to a second thickness $T_2$, the corrodible material 710 may become increasingly curved under the pressure P. The corrosive environment may have a relatively higher pressure than an interior of the Fabry-Perot cavity 702, and the net pressure P may cause the corrodible material 710 to curve inward toward the at least one optical fiber 706. The corrodible material 710 having the first thickness $T_1$ may be positioned a first distance $L_1$ from the distal end 704 of the at least one optical fiber 706 under the pressure P (FIG. 7B). As the corrodible material 710 corrodes, the thickness of the corrodible material 710 may be reduced to the second thickness $T_2$ (FIG. 7C). The corrodible material 710 with the second thickness $T_2$ may be less resistant to curving compared to the corrodible material 710 with the first thickness $T_1$, due to a loss of mass and physical structure. Due to the increased curvature of the corrodible material 710, an interior surface of the corrodible material 710 may be positioned a second distance $L_2$ closer to the distal end 704 of the at least one optical fiber 706 compared to the first distance $L_1$. The change in curvature of the corrodible material 710 may affect a light signal transmitted through the at least one optical fiber 706. Thus, changes in the light signal may be measured and analyzed to determine corrosion of the corrodible material 710, such as by an analysis module 116 (FIG. 1) (in the form of, e.g., an interferometer, a light wavelength sensor, a light intensity sensor).

Accordingly, the fiber optic sensor 700 may be used to determine a corrosion rate and/or corrosion amount of the corrodible material 710. In turn, the corrosion of the corrodible material 710 may be correlated to corrosion of a downhole component, as described above.

Figures 8A, 8B:
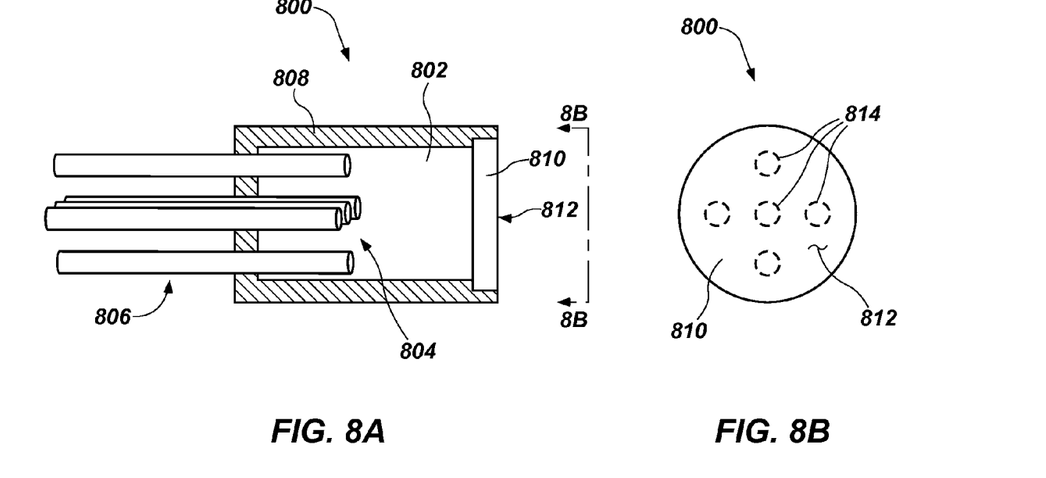
FIG. 8A shows a partial cross-sectional side view of another embodiment of a fiber optic sensor according to the present disclosure, including multiple optical fibers.
FIG. 8B shows an end view of the fiber optic sensor of FIG. 8A, taken from line 8B-8B in FIG. 8A.

Referring to FIGS. 8A and 8B, in some embodiments, a fiber optic sensor 800 for wellbore sensing systems of the present disclosure may include a Fabry-Perot cavity 802 at a distal end 804 of a plurality of optical fibers 806. The Fabry-Perot cavity 802 may be defined by a tube 808 capped with a corrodible material 810 having an external surface 812 that is configured for exposure to a corrosive environment, such as a fluid environment of oil and gas exploration or production (e.g., within a subterranean borehole). The fiber optic sensor 800 of FIGS. 8A and 8B may generally be configured and operate similar to the fiber optic sensor 700 of FIG. 7A-7C. However, the plurality of optical fibers 806 may enable simultaneous or sequential measurement of multiple portions of the corrodible material 810.

For example, each optical fiber of the plurality of optical fibers 806 (FIG. 8A) may be used to measure corrosion at a unique region 814 (FIG. 8B) of the external surface 812 of the corrodible material 810. Thus, in addition to being used to measure overall corrosion, the fiber optic sensor 800 including a plurality of optical fibers 806 may be used to measure non-uniform corrosion, such as pitting, localized corrosion, and corrosion gradients.

Figure 9:
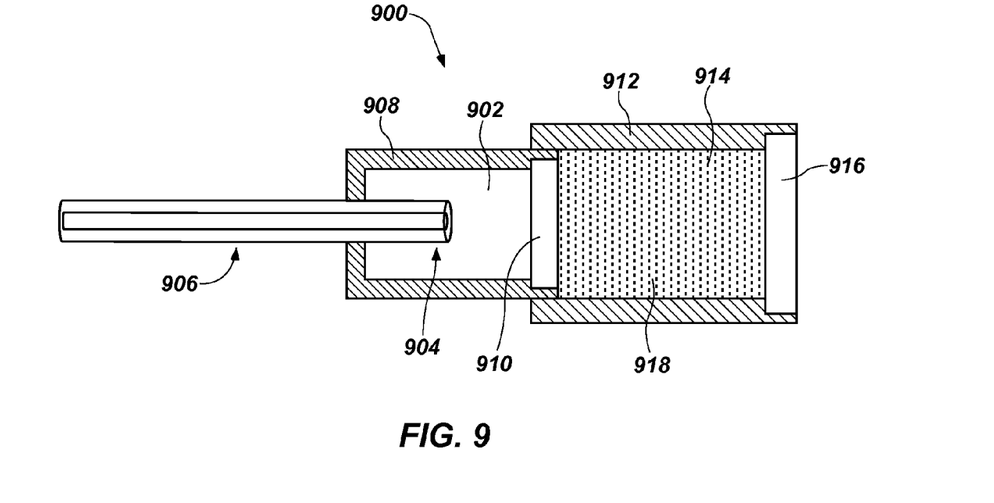
FIG. 9 shows a partial cross-sectional side view of another embodiment of a fiber optic sensor according to the present disclosure.

Referring to FIG. 9, wellbore sensing systems of the present disclosure may include a fiber optic sensor 900 including a Fabry-Perot cavity 902 at a distal end 904 of at least one optical fiber 906. The Fabry-Perot cavity 902 may be defined by a first tube 908 capped with an inert diaphragm 910. A second tube 912 may be coupled to the first tube 908. The second tube 912 may define a cavity 914 between the inert diaphragm 910 and a corrodible diaphragm 916. The cavity 914 defined by the second tube 912 may be filled with an inert fluid 918, such as a liquid (e.g., oil) or a gas.

The inert diaphragm 910 of the fiber optic sensor 900 of FIG. 9 may not be a same or similar material to a downhole component. By way of example and not limitation, the inert diaphragm 910 may include one or more of a ceramic material, a diamond-like carbon ("DLC") material, an oxide material, a sapphire material, an alumina material, and a silicon carbide material. The corrodible diaphragm 916 may be or include a material that is similar to or the same as a downhole component. For example, the corrodible diaphragm 916 may include one or more of a carbon steel, a tool steel, a stainless steel, and a so-called "corrosion resistant alloy" (i.e., a mixture of various metals, such as stainless steel, chrome, nickel, iron, copper, cobalt, molybdenum, tungsten, and/or titanium).

The fiber optic sensor 900 of FIG. 9 may operate similarly to the fiber optic sensor 700 of FIG. 7A-7C, except that the inert diaphragm 910 defining the Fabry-Perot cavity 902 and capping the first tube 908 may not be corroded during use. Rather, the corrodible diaphragm 916 of the second tube 912 may be corroded during use, which may increase a pressure on the inert fluid 918, which, in turn, may increase pressure on the inert diaphragm 910 and result in the inert diaphragm 910 curving toward the distal end 904 of the at least one optical fiber 906. The curvature of the inert diaphragm 910 may be measured, and the curvature may be correlated to corrosion of the corrodible diaphragm 916 and further correlated to corrosion of a downhole component. Thus, the fiber optic sensor 900 may be used to sense corrosion without consumption of the inert diaphragm 910 defining the Fabry-Perot cavity 902.

Figure 10A:
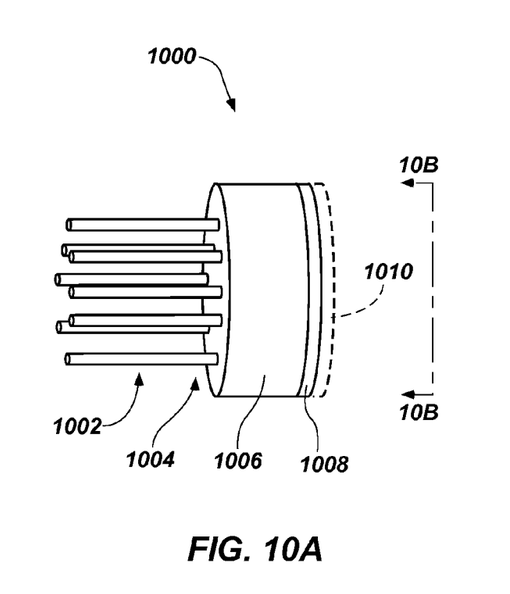
FIG. 10A shows a partial cross-sectional side view of another embodiment of a fiber optic sensor according to the present disclosure.
Figure 10B:
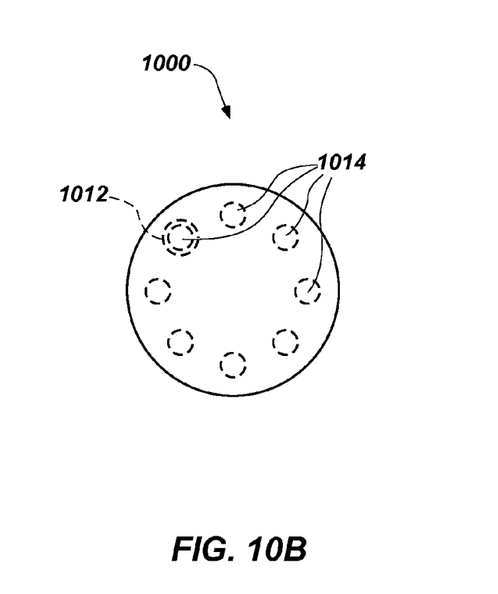
FIG. 10B shows an end view of the fiber optic sensor of FIG. 10A, taken from line 10B-10B in FIG. 10A.

Referring to FIGS. 10A and 10B, wellbore sensing systems of the present disclosure may include a fiber optic sensor 1000 including a plurality of optical fibers 1002 having respective distal ends 1004. Optionally, the distal ends 1004 of the plurality of optical fibers 1002 may be coupled to (e.g., disposed within) a transparent material 1006 (e.g., an epoxy material). A sensor material 1008 may be disposed over or proximate to the distal ends 1004 of the plurality of optical fibers 1002, such as on a surface of the transparent material 1006 opposite the plurality of optical fibers 1002. The sensor material 1008 may be a corrodible material that is the same as material of a downhole component, such that corrosion of the sensor material 1008 may be correlated to corrosion of the downhole component. Optionally, in some embodiments, a mask material 1010 (as shown by dashed line) including at least one aperture 1012 therethrough may cover at least a portion of the sensor material 1008.

Fabry-Perot interferometry for measuring corrosion has been generally described in U.S. patent application Ser. No. 08/194,294 to Sirkis, titled "FIBER OPTIC STRESS-CORROSION SENSORY AND SYSTEM," filed Feb. 9, 1994, now U.S. Pat. No. 5,367,583 ("the '583 patent"), the entire disclosure of which is incorporated herein by reference. The fiber optic sensor 1000 may operate on the principle that a thickness of thin films may affect a reflectance of the thin film, as discussed in the '583 patent incorporated by reference above. Accordingly, corrosion of the sensor material 1008 may result in a change in reflectance of the sensor material 1008 that can be measured using the plurality of optical fibers 1002. Alternatively or additionally, the fiber optic sensor 1000 may operate on a principle that a change in the thickness of the sensor material 1008 results in a change in a distance between the sensor material 1008 and the distal ends 1004 of the plurality of optical fibers 1002, as discussed above in relation to FIGS. 7A through 7C. Accordingly, corrosion of the sensor material 1008 may result in a change in the interference pattern that can be measured using the plurality of optical fibers 1002. In some embodiments, an entire surface of the sensor material 1008 may be exposed to a corrosive environment, and the optical fibers 1002 may be used to sense a change in thickness of respective regions 1014 of the sensor material 1008. In such embodiments, the plurality of optical fibers 1002 may be used to sense uniform and non-uniform corrosion (e.g., pitting, localized corrosion, corrosion gradients) at the respective regions 1014 of the sensor material 1008.

In some embodiments, the sensor material 1008 may have a variable thickness such that each of the regions 1014 of the sensor material 1008 has a different thickness than other regions 1014. Initially, a first one of the regions 1014 may have a thickness that is at or below a thickness that renders a reflectance of the first region 1014 sensitive to a reduction in thickness of the sensor material 1008 at the first region 1014. A second region 1014 may have an initial thickness that is twice the initial thickness of the first region 1014. Accordingly, as both of the first and second regions 1014 corrode, the first region 1014 may corrode entirely away as the second region 1014 reaches a thickness for which reflectivity is sensitive to additional corrosion. A third region 1014 may have an initial thickness that is three times the initial thickness of the first region 1014, such that as the second region 1014 corrodes entirely away, the third region 1014 reaches a thickness for which reflectivity is sensitive to yet additional corrosion. Other regions 1014 may similarly have unique thicknesses. By way of example and not limitation, the first region 1014 may have an initial thickness of about 5 µm, the second region 1014 may have an initial thickness of about 10 µm, the third region 1014 may have an initial thickness of about 15 µm, etc. In such embodiments, the fiber optic sensor 1000 may be used for a greater period of time and after further corrosion compared to a similar sensor that has a uniform thickness.

Although embodiments of the fiber optic sensor 1000 have been described as including a single, common sensor material 1008 that is sensed by the plurality of optical fibers 1002, the present disclosure is not so limited. Alternatively, a separate sensor material 1008 may be disposed on a distal end 1004 of each optical fiber of the plurality of optical fibers 1002. Each of the separate sensor materials 1008 may have a different thickness, similar to the different thicknesses of the regions 1014 described above. By way of another example and not limitation, each of the separate sensor materials 1008 may have an initial thickness that is about 5 µm or less.

In some embodiments, the mask material 1010 may be used to cover one or more of the regions 1014 of the sensor material 1008 and protect the one or more of the regions 1014 from corrosion. The aperture 1012 may be used to expose at least one of the regions 1014 to a corrosive environment. An optical fiber 1002 associated with the exposed region 1014 may be used to measure corrosion of the sensor material 1008. After the sensor material 1008 at the exposed region 1014 is at least partially consumed by the corrosion, the mask material 1010 may be rotated or otherwise moved relative to the sensor material 1008 to expose another region 1014. Then, another optical fiber 1002 associated with the exposed other region 1014 may be used to measure corrosion of the sensor material 1008. This process may be repeated until all of the regions 1014 are exposed and at least partially consumed by corrosion. In such embodiments, the sensor 1000 may be used for a greater period of time and after further corrosion compared to a similar sensor that lacks the mask material 1010. A mask material 1010 as described may also be used with other embodiments that include a plurality of optical fibers, such as with the embodiment shown and described in connection with FIGS. 8A and 8B.

In some embodiments, the present disclosure includes wellbore sensing systems that include multiple fiber optic sensors and, optionally, at least one reference sensor. For example, multiple fiber optic sensors 200 like that described with reference to FIG. 2 may be used together, with each fiber optic sensor 200 including a mass of sensor material 208 different from other fiber optic sensors 200. Thus, a first fiber optic sensor 200 may include a first mass of sensor material 208 that includes a first corrodible material and a second fiber optic sensor 200 may include a second mass of sensor material that includes a second corrodible material different from the first corrodible material. Alternatively or additionally, a third fiber optic sensor 200 may include a third mass of sensor material 208 that includes an inert material that is susceptible to scale deposition. One or more reference fiber optic sensors 300, as described above with reference to FIG. 3, may be used in combination with the multiple fiber optic sensors.

Similarly, other embodiments of sensors and systems described above may be combined in various ways to provide a wellbore sensing system for sensing one or multiple conditions within a wellbore. Such a system may include multiple sensors selected from the following list, for example: one or more fiber optic sensors 200, one or more reference fiber optic sensors 300, one or more multi-point sensors 400, one or more reference optical fibers 602, one or more fiber optic sensors 700, one or more fiber optic sensors 800, one or more fiber optic sensors 900, and one or more fiber optic sensors 1000 (described above with reference to FIGS. 2 through 10B).

Additional non-limiting example embodiments of the present disclosure are set forth below.

Embodiment 1: A wellbore sensing system, comprising: a tube defining a Fabry-Perot cavity; an optical fiber comprising a distal end disposed within the Fabry-Perot cavity and a proximal end opposite the distal end; a corrodible material capping the Fabry-Perot cavity; and an analysis module operatively coupled to the proximal end of the optical fiber, the analysis module configured to sense and analyze a difference of a light signal resulting from a change in a distance between the corrodible material and the distal end of the optical fiber due to a change in thickness of the corrodible material.

Embodiment 2: The system of Embodiment 1, wherein the tube is positioned proximate a downhole component within a wellbore.

Embodiment 3: The system of Embodiment 1 or Embodiment 2, wherein the distal end of the optical fiber is mounted to an electrical submersible pump.

Embodiment 4: The system of any one of Embodiments 1 through 3, wherein the corrodible material is selected from the group consisting of aluminum, titanium, a carbon steel, a tool steel, a stainless steel, and a corrosion resistant alloy.

Embodiment 5: The system of any one of Embodiments 1 through 4, further comprising a reference sensor including a distal end free of the corrodible material.

Embodiment 6: The system of Embodiment 5, wherein the reference sensor comprises: another tube defining another Fabry-Perot cavity; at least one other optical fiber comprising a distal end disposed within the another Fabry-Perot cavity; and an inert material capping the another Fabry-Perot cavity.

Embodiment 7: The system of Embodiment 6, wherein the inert material capping the Fabry-Perot cavity of the reference sensor comprises one or more of a ceramic material, a diamond-like carbon material, an oxide material, a sapphire material, an alumina material, a silicon carbide material, a silicon material, and a metallic material coated with the inert material.

Embodiment 8: The system of any one of Embodiments 1 through 7, wherein the analysis module further comprises a light source, a photodetection and signal processing interferometer coupled to a proximal end of the plurality of optical fibers and an output configured to provide a signal corresponding to a corrosion rate of the corrodible material.

Embodiment 9: A device for sensing corrosion of downhole equipment, the device comprising: at least one optical fiber comprising a distal end and a proximal end; a corrodible material disposed over the distal end of the at least one optical fiber; and an analysis module operatively coupled to the proximal end of the at least one optical fiber, the analysis module configured to sense and analyze differences in a light signal reflecting from the corrodible material.

Embodiment 10: The device of Embodiment 9, wherein the at least one optical fiber comprises a plurality of optical fibers, wherein a separate corrodible material is disposed over a respective distal end of each optical fiber of the plurality of optical fibers, wherein each of the separate corrodible materials comprises a different thickness from other separate corrodible materials.

Embodiment 11: The device of Embodiment 10, wherein an initial thickness of each of the separate corrodible materials is about 5 µm or less.

Embodiment 12: The device of any one of Embodiments 9 through 11, wherein the analysis module comprises at least one of an interferometer, a light intensity sensor, and a light wavelength sensor.

Embodiment 13: The device of any one of Embodiments 9 through 12, wherein the distal end of the at least one optical fiber is disposed within a transparent epoxy material, wherein the corrodible material coats a surface of the transparent epoxy material, further comprising a mask with an aperture therethrough, the mask covering the corrodible material, the mask and aperture configured to selectively expose a region of the corrodible material corresponding to the at least one optical fiber.

Embodiment 14: A system for sensing at least one condition in oil and gas exploration or production equipment, the system comprising: at least one optical fiber comprising a distal end, at least one fiber Bragg grating proximate the distal end, and a proximal end; an analysis module operatively coupled to the proximal end of the at least one optical fiber, the analysis module configured to sense and analyze variations in light reflected from the at least one fiber Bragg grating; and a mass of sensor material coupled to the distal end of the at least one optical fiber, at least one surface of the mass of sensor material exposed to an environment surrounding the distal end of the at least one optical fiber, wherein the distal end of the at least one optical fiber with the mass of sensor material coupled thereto is suspended from above the at least one fiber Bragg grating to induce stress on the at least one fiber Bragg grating due to a weight of the mass of sensor material.

Embodiment 15: The system of Embodiment 14, wherein the mass of sensor material consists essentially of a mass of corrodible material.

Embodiment 16: The system of Embodiments 14 or Embodiment 15, further comprising at least one reference optical fiber comprising a distal end including a fiber Bragg grating and a mass of inert material coupled to the distal end of the at least one reference optical fiber.

Embodiment 17: The system of Embodiment 16, wherein the distal end of the at least one reference optical fiber is positioned adjacent to the distal end of the at least one optical fiber.

Embodiment 18: The system of Embodiment 16 or Embodiment 17, wherein the mass of inert material comprises at least one of a ceramic material, a diamond-like carbon material, an oxide material, a sapphire material, an alumina material, a silicon carbide material, a silicon material, and a mass of metallic material coated with the inert material.

Embodiment 19: The system of any one of Embodiments 14 through 18, wherein the mass of sensor material is selected to be at least substantially the same as a material of a surface of a downhole component to be exposed to a same environmental condition as the mass of sensor material during disposition of the mass of sensor material and the downhole component in a wellbore.

Embodiment 20: The system of any one of Embodiments 14 through 19, further comprising a housing covering lateral sides of the mass of sensor material.

Embodiment 21: The system of Embodiment 20, wherein the housing is coupled to a downhole component.

Embodiment 22: The system of any one of Embodiments 14 through 21, further comprising a substrate of inert material coupled to the at least one optical fiber proximate the distal end of the at least one optical fiber, wherein the mass of corrodible material is coupled to the substrate.

Embodiment 23: The system of any one of Embodiments 14 through 22, wherein the at least one optical fiber comprises a plurality of optical fibers each comprising a distal end including a fiber Bragg grating and each coupled to the mass of corrodible material.

Embodiment 24: A device for sensing deposition of material on downhole equipment, the device comprising: at least one optical fiber comprising a proximal end and a distal end including a fiber Bragg grating; an analysis module operatively coupled to the proximal end of the at least one optical fiber, the analysis module configured to sense and analyze variations in light reflected from the at least one fiber Bragg grating; a suspension element coupled to the at least one optical fiber above the fiber Bragg grating; and a mass of inert material coupled to the at least one optical fiber below the fiber Bragg grating and suspended from the suspension element by the distal end of the at least one optical fiber.

Embodiment 25: The device of Embodiment 24, further comprising: at least one reference optical fiber comprising a distal end including a fiber Bragg grating; and a mass of material coupled to the at least one reference optical fiber proximate the distal end of the at least one reference optical fiber, at least an exposed portion of the mass of material being selected to resist deposition of scale thereon.

Embodiment 26: A system for sensing at least one condition in a subterranean wellbore, the system comprising: at least one optical fiber comprising a distal end, a plurality of fiber Bragg gratings along a length thereof, and a proximal end; a plurality of sensor materials coupled to the at least one optical fiber and surrounding respective fiber Bragg gratings of the plurality of fiber Bragg gratings; and a light wavelength sensor coupled to a proximal end of the at least one optical fiber, the light wavelength sensor configured to sense a wavelength of light reflected from the plurality of fiber Bragg gratings.

Embodiment 27: The system of Embodiment 26, wherein the plurality of sensor materials comprises a material selected to react with a reactive chemical.

Embodiment 28: The system of Embodiment 27, wherein the reactive chemical comprises $H_2S$.

Embodiment 29: The system of Embodiment 27 or Embodiment 28, wherein the material selected to react with a reactive chemical comprises a metal oxide material.

Embodiment 30: The system of any one of Embodiments 27 through 29, wherein the material selected to react with a reactive chemical comprises $ZnO$.

Embodiment 31: The system of Embodiment 26, wherein the plurality of sensor materials comprises a pre-stressed corrodible material.

Embodiment 32: The system of any one of Embodiments 26 through 31, further comprising at least one reference optical fiber extending along the length of the at least one optical fiber.

Embodiment 33: The system of any one of Embodiments 26 through 32, wherein the plurality of fiber Bragg gratings is spaced along the length of the at least one optical fiber at intervals of at least about 5 mm.

Embodiment 34: A wellbore sensing system, comprising: a first device for sensing corrosion of downhole equipment according to Embodiment 9 and comprising a first corrodible material disposed over the distal end of at least one first optical fiber; and a second device for sensing corrosion of downhole equipment according to Embodiment 9 and comprising a second corrodible material different from the first corrodible material disposed over a distal end of at least one second optical fiber.

Embodiment 35: The system of any one of Embodiments 1 through 8, further comprising at least one additional optical fiber comprising a distal end disposed within the Fabry-Perot cavity, wherein a separate corrodible material is disposed over a respective distal end of each of the optical fiber and the at least one additional optical fiber, wherein each of the separate corrodible materials comprises a different thickness from other separate corrodible materials.

Embodiment 36: The system of any one of Embodiments 1 through 8, further comprising: at least one additional optical fiber comprising a distal end disposed within the Fabry-Perot cavity; and a mask with an aperture therethrough, the mask covering the corrodible material, the mask and aperture configured to selectively expose respective regions of the corrodible material corresponding to the optical fiber and the at least one additional optical fiber.

The embodiments of the disclosure described above and illustrated in the accompanying drawing figures do not limit the scope of the invention, since these embodiments are merely examples of embodiments of the disclosure. The invention is encompassed by the appended claims and their legal equivalents. Any equivalent embodiments lie within the scope of this disclosure. Indeed, various modifications of the present disclosure, in addition to those shown and described herein, such as other combinations and modifications of the elements described, will become apparent to those of ordinary skill in the art from the description. Such embodiments, combinations, and modifications also fall within the scope of the appended claims and their legal equivalents.

What is claimed is:

1. A device for sensing corrosion of downhole equipment, the device comprising:
   at least one optical fiber comprising a distal end, at least one fiber Bragg grating proximate the distal end, and a proximal end;
   a mass of corrodible sensor material coupled to the distal end of the at least one optical fiber, at least one surface of the mass of corrodible sensor material exposed to an environment surrounding the distal end of the at least one optical fiber; and an analysis module operatively coupled to the proximal end of the at least one optical fiber, the analysis module configured to sense and analyze differences in a light signal reflecting from the at least one fiber Bragg grating, wherein the distal end of the at least one optical fiber with the mass of corrodible sensor material coupled thereto is suspended from above the at least one fiber Bragg grating to induce stress on the at least one fiber Bragg grating due to a weight of the mass of sensor material.

2. The device of claim 1, wherein the at least one optical fiber comprises a plurality of optical fibers, wherein a separate mass of corrodible sensor material is disposed over a respective distal end of each optical fiber of the plurality of optical fibers, wherein each of the separate masses of corrodible sensor materials comprises a different thickness from other separate masses of corrodible sensor materials.

3. The device of claim 2, wherein an initial thickness of each of the separate masses of corrodible sensor materials is about 5 µm or less.

4. The device of claim 1, wherein the analysis module comprises at least one of an interferometer, a light intensity sensor, and a light wavelength sensor.

5. The device of claim 1, wherein the distal end of the at least one optical fiber is disposed within a transparent epoxy material, wherein the mass of corrodible sensor material coats a surface of the transparent epoxy material, further comprising a mask with an aperture therethrough, the mask covering the mass of corrodible sensor material, the mask and aperture configured to selectively expose a region of the mass of corrodible sensor material corresponding to the at least one optical fiber.

6. A system for sensing at least one condition in oil and gas exploration or production equipment, the system comprising:

at least one optical fiber comprising a distal end, at least one fiber Bragg grating proximate the distal end, and a proximal end;

an analysis module operatively coupled to the proximal end of the at least one optical fiber, the analysis module configured to sense and analyze variations in light reflected from the at least one fiber Bragg grating; and a mass of sensor material coupled to the distal end of the at least one optical fiber, at least one surface of the mass of sensor material exposed to an environment surrounding the distal end of the at least one optical fiber, wherein the distal end of the at least one optical fiber with the mass of sensor material coupled thereto is suspended from above the at least one fiber Bragg grating to induce stress on the at least one fiber Bragg grating due to a weight of the mass of sensor material.

7. The system of claim 6, wherein the mass of sensor material consists essentially of a mass of corrodible material.

8. The system of claim 6, further comprising at least one reference optical fiber comprising a distal end including a fiber Bragg grating and a mass of inert material coupled to the distal end of the at least one reference optical fiber.

9. The system of claim 8, wherein the distal end of the at least one reference optical fiber is positioned adjacent to the distal end of the at least one optical fiber.

10. The system of claim 8, wherein the mass of inert material comprises at least one of a ceramic material, a diamond-like carbon material, an oxide material, a sapphire material, an alumina material, a silicon carbide material, a silicon material, and a mass of metallic material coated with the inert material.

11. The system of claim 6, wherein the mass of sensor material is selected to be at least substantially the same as a material of a surface of a downhole component to be exposed to a same environmental condition as the mass of sensor material during disposition of the mass of sensor material and the downhole component in a wellbore.

12. The system of claim 6, further comprising a housing covering lateral sides of the mass of sensor material.

13. The system of claim 12, wherein the housing is coupled to a downhole component.

14. The system of claim 6, further comprising a substrate of inert material coupled to the at least one optical fiber proximate the distal end of the at least one optical fiber, wherein the mass of corrodible material is coupled to the substrate.

15. The system of claim 6, wherein the at least one optical fiber comprises a plurality of optical fibers each comprising a distal end including a fiber Bragg grating and each coupled to the mass of corrodible material.

16. A system for sensing deposition of material on downhole equipment, the system comprising:

a plurality of optical fibers comprising a proximal end and a distal end including at least one fiber Bragg grating;

an analysis module operatively coupled to the proximal end of each of the plurality of optical fibers, the analysis module configured to sense and analyze variations in light reflected from the at least one fiber Bragg grating;

a suspension element coupled to each of the plurality of optical fibers above the fiber Bragg grating;

a mass of inert material coupled to a first optical fiber of the plurality below the at least one fiber Bragg grating and suspended from the suspension element by the distal end of the at least one optical fiber; and a mass of sensor material coupled to the distal end of a second optical fiber of the plurality, at least one surface of the mass of sensor material exposed to an environment surrounding the distal end of the second optical fiber of the plurality, wherein the distal end of the second optical fiber of the plurality with the mass of sensor material coupled thereto is suspended from the suspension element above the at least one fiber Bragg grating to induce stress on the at least one fiber Bragg grating due to a weight of the mass of sensor material.

17. The system of claim 16, wherein the mass of inert material coupled to the first optical fiber is selected to resist deposition of scale thereon.

* * * * *

UNITED STATES PATENT AND TRADEMARK OFFICE
CERTIFICATE OF CORRECTION

Page 1 of 1

PATENT NO. : 9,562,844 B2
APPLICATION NO. : 14/319158
DATED : February 7, 2017
INVENTOR(S) : Anusha Chilukuri and Othon R. Monteiro It is certified that error appears in the above-identified patent and that said Letters Patent is hereby corrected as shown below:

In the Specification

| Column 8,  | Line 65, | change "$H_2S$ to foini" to --$H_2S$ to form-- |
| Column 10, | Line 43, | change "of FIG. 7A-7C." to --of FIGS. 7A-7C.-- |
| Column 11, | Line 12, | change "of FIG. 7A-7C," to --of FIGS. 7A-7C,-- |

Signed and Sealed this
Fifth Day of December, 2017

Joseph Matal
*Performing the Functions and Duties of the
Under Secretary of Commerce for Intellectual Property and
Director of the United States Patent and Trademark Office*